United States Patent [19]

Kosegaki et al.

[11] Patent Number: 4,569,736

[45] Date of Patent: Feb. 11, 1986

[54] MEDICAL INSTRUMENTS MADE FROM A POLYOLEFIN COMPOSITION WHICH HAS BEEN STERILIZED WITH GAMMA IRRADIATION

[75] Inventors: Kimiho Kosegaki; Ryushiro Takeshita, both of Yokkaichi; Kazuhiko Kobayashi, Ibaragi, all of Japan

[73] Assignee: Terumo Kabushiki Kaisha, Tokyo, Japan

[21] Appl. No.: 591,884

[22] Filed: Mar. 21, 1984

Related U.S. Application Data

[63] Continuation of Ser. No. 418,289, Sep. 15, 1982, abandoned.

[51] Int. Cl.$^4$ ................................................ C08K 5/52
[52] U.S. Cl. ........................... 523/105; 524/101; 524/102; 524/128; 524/342; 604/187; 422/22
[58] Field of Search ............... 204/159.2; 524/101, 524/102, 128, 342; 523/300

[56] References Cited

U.S. PATENT DOCUMENTS

| | | | |
|---|---|---|---|
| 3,196,185 | 7/1965 | Ranson | 524/342 |
| 3,356,770 | 12/1967 | Larrison | 524/128 |
| 3,476,699 | 11/1969 | Kauder et al. | 524/114 |
| 3,940,325 | 2/1976 | Hirao | 524/232 |
| 4,210,577 | 7/1980 | Minagawa et al. | 524/103 |
| 4,221,700 | 9/1980 | Minagawa et al. | 524/128 |
| 4,233,412 | 11/1980 | Rody et al. | 528/289 |
| 4,314,039 | 2/1982 | Kawai et al. | 524/108 |
| 4,401,536 | 8/1983 | Lundell et al. | 204/159.2 |

FOREIGN PATENT DOCUMENTS

7736A1 10/1980 European Pat. Off. .

OTHER PUBLICATIONS

Norman S. Allen "Catalytic Thermal Oxidation of Phenolic Antioxidants by Hindered Piperidine Compounds", Polymer Degradation and Stability 3 (1980–1981), 73–81.
Khirud B. Chakraborty et al., "Mechanisms of Antioxidant Action: The Behavior of Hindered Piperidine Stabilizers During Processing of LDPE", Chemistry & Industry, 237–238 (Apr. 1, 1978).
J. L. Williams et al., "Stability of Gamma Irradiated Polypropylene, Part I, Mechanical Properties", Polymer Preprints, vol. 18, No. 1 (Mar. 1977) 410–413.
T. S. Dunn et al., "Stability of Gamma Irradiated Polypropylene Part II, Electron Spin Resonance Studies", Polymer Preprints, vol. 18, No. 1, (Mar. 1977), 414–419.
J. Reid Shelton, "Stabilization Fundamentals in Thermal Autoxidation of Polymers", Stabilization and Degradation of Polymers–David Allara et al., editors, American Chemical Society, Wash., D.C. 215–225 (1978).

*Primary Examiner*—Veronica P. Hoke
*Attorney, Agent, or Firm*—Frishauf, Holtz, Goodman & Woodward

[57] ABSTRACT

YMedical instruments, e.g., syringes, which can be sterilized by gamma irradiation and which are made of polyolefin resins (preferably a polypropylene polymer) which are resistant to gamma irradiation. The polyolefin is compounded with a specific hindered amine and a specific phenol or its phosphorous ester, each in an amount of from 0.01 to 1 part by weight per 100 parts of the polyolefin.

12 Claims, No Drawings

MEDICAL INSTRUMENTS MADE FROM A POLYOLEFIN COMPOSITION WHICH HAS BEEN STERILIZED WITH GAMMA IRRADIATION

This application is a continuation of application Ser. No. 418,289, filed Sept. 15, 1982, now abandoned.

BACKGROUND OF THE INVENTION

1. Field of the Invention

This invention relates to polyolefin compositions resistant to gamma irradiation and medical instruments made thereof.

More particularly, it is concerned with polyolefin compositions stabilized to gamma irradiation by incorporating specific stabilizers and medical instruments made thereof.

Polyolefins, particularly polypropylenes are often molded into medical instruments. These molded materials, however, deteriorate when subjected to sterilization by gamma irradiation thereby resulting in cracking and/or yellow discoloration which causes problems in practical use.

2. Description of the Prior Art

As the method to prevent the deterioration of polyolefins by gamma irradiation, the use of hindered amines as the additive is known as disclosed in Japanese Patent Laid Open No. 19199/80. Such a method, however, has not been satisfactory in terms of preventing deterioration with lapse of time after gamma irradiation.

As a result of extensive studies to provide a solution to this problem, we have found that the deterioration with lapse of time after gamma irradiation is effectively prevented simultaneously with less discoloration produced by providing compositions containing a polyolefin with a specific hindered amine and a specific phenol or its phosphorous ester and medical instruments made thereof.

SUMMARY OF THE INVENTION

It is therefore an object of this invention to provide polyolefin compositions with improved resistance to gamma irradiation.

Another object of this invention is to provide medical instruments, particularly syringes stable when subjected to sterilization by gamma irradiation.

According to the present invention, there are provided polyolefin compositions resistant to gamma irradiation comprising a hindered amine compound represented by the formula [I] or [II] below and a phenol or a phosphorous ester thereof represented by any one of the formulae [III]–[VI] below incorporated respectively in a proportion from 0.01 to 1 part by weight per 100 parts by weight of the polyolefin.

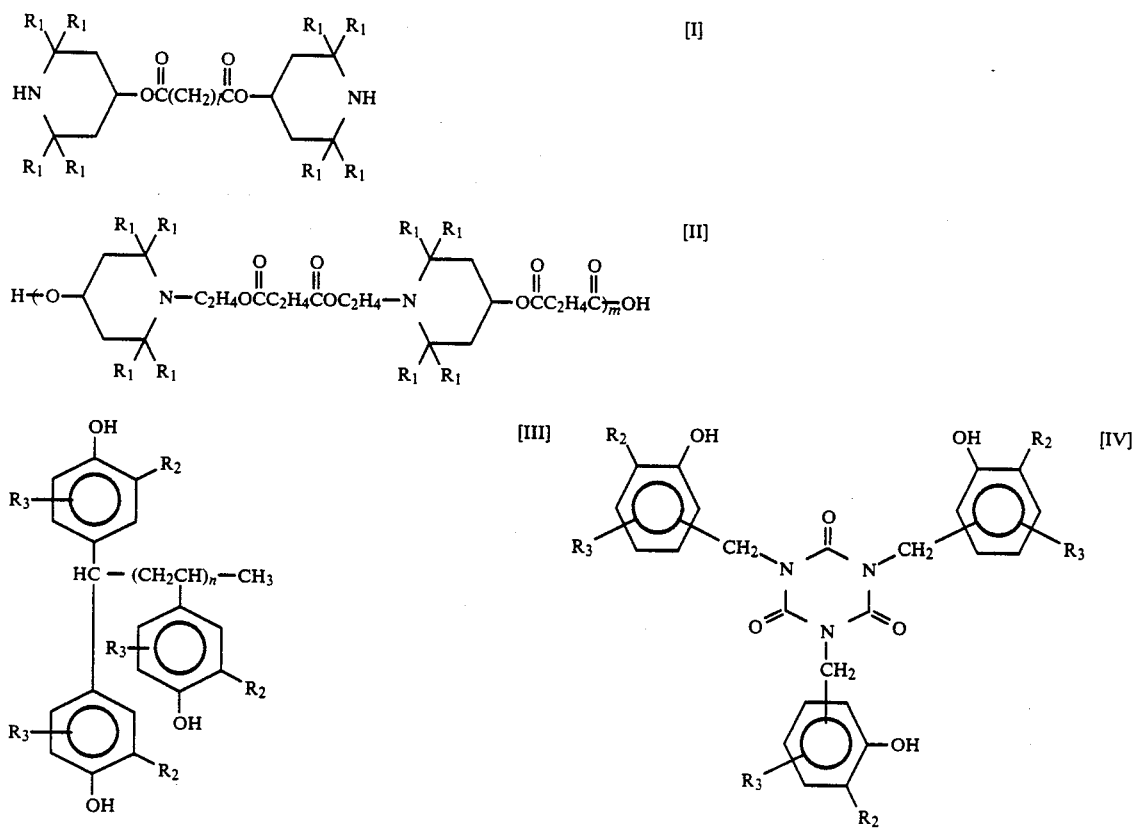

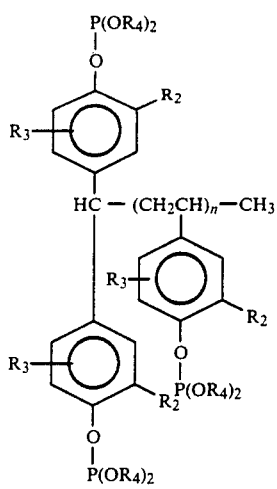

[V]

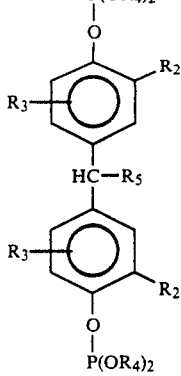

[VI]

In the foregoing formulae, $R_1$ and $R_3$ represent an alkyl group containing from 1 to 18 carbon atoms respectively, $R_2$ and $R_5$ represent an alkyl group containing from 1 to 8 carbon atoms respectively, $R_4$ represents an alkyl group containing from 1 to 30 carbon atoms, 1 is an interger from 0 to 30, m is an integer from 1 to 40, and n is an integer from 1 to 6.

Furthermore, the present invention provides medical instruments made of the above-described compositions.

As the composition according to the invention are resistant to gamma irradiation, they are applicable to the use as vessels for use in the gamma irradiation equipment and the like in addition to the use as medical instruments.

The medical instruments of the invention are suitable for use after sterilization by gamma irradiation. As preferred examples of the medical instruments for such use are mentioned polyolefin, particularly polypropylene syringes.

As the polyolefins usable in the present invention may be mentioned homo- or copolymers of α-olefins such as ethylene, propylene, butene, pentene, hexene, 4-methylpentene, heptene, octene and the like; random, block or graft copolymers of a major portion by weight of these α-olefins with vinyl esters such as vinyl acetate and the like, unsaturated organic acids such as acrylic acid, maleic anhydride, methyl methacrylate and the like including the salts, amides and amines, and vinylsilanes such as vinyltrimethoxysilane and the like; or modified ones of these polymers by the treatment such as chlorination, sulfonation or oxidation.

In an embodiment, for example, low-, medium- or high-density polyethylene, polypropylene, polybutene, ethylene-propylene random- or block copolymer, ethylene-propylenebutenecopolymer, ethylene-butene copolymer, ethylene-4-methylpentene copolymer, propylene-hexene copolymer, propylene-hexene-butene copolymer or the like is employed.

Among these polymers, particularly effective are propylene polymers such as polypropylene, propylene-ethylene randaom or block copolymer, propylene-ethylene-butene copolymer, propylene-hexene-butene copolymer and the like.

The hindered amines employed in the present invention are those having the above-mentioned formula [I] or [II].

Preferred examples of those represented by the formula [I] are bis(2,2,6,6-tetramethylpiperidyl)adipate, bis(2,2,6,6-tetramethylpiperidyl)sebacate, bis(2,2,6,6-tetramethylpiperidyl)fumarate and the like.

As an example of those represented by the formula [II] is mentioned a compound in which $R_1$ is methyl and m is 4.

These hindered amines may be employed alone or incombination of the two or more.

The phenols or phosphorous ester compounds thereof employed in the invention are those having the structure shown by any one of the aforementioned formulae [III]–[VI].

A preferred example of the compounds represented by the formula [III]]is 1,1,3-tris(2-methyl-4-hydroxy-5-t-butylphenyl)butane. As a preferred example of the compounds represented by the formula [IV] is mentioned tris(3,5-di-t-butyl-4-hydroxybenzyl)isocyanurate. Preferred examples of the compounds [V] and [VI] are compounds in which $R_2$ is methyl, $R_3$ is t-butyl at 2-position, $R_4$ is —$C_{13}H_{27}$ and $R_5$ is —$C_3H_7$.

These phenols or the phosphorous ester compounds thereof may be employed alone or in combination of the two or more.

These components are incorporated in a proportion from 0.01 to 1 part by weight, preferably from 0.01 to 0.5 part by weight of the hindered amines represented by the aforementioned formula [I] or [II] and the phenols or their phosphorous ester compounds represented by any one of the formulae [III]–[VI] respectively per 100 parts by weight of the polyolefins.

Use of the ratio below 0.01 part by weight will not produce satisfactory results. On the other hand, use of the ratio in excess of 1 part by weight will not further improve the results and therefore is impractical though being acceptable.

Other additive components may be added to the compositions of the invention. Such additive components include conventional antioxidants, polymer clarifiers, nucleating agents, ultraviolet light absorbers, lubricants, antistatic agents, antiblocking agents, anti-dripping agents, pigments, peroxides, dispersing agents such as metal soap, neutralizing agents and the like.

Examples of the antioxidants are 3,5-di-t-butyl-4-hydroxytoluene, tetrakis[methylene-3-(3,5-di-t-butyl-4-hydroxyphenyl)propionate]methane and the like. The antioxidant, however, is preferably added in a small proportion, because it may cause yellow discoloration.

On the other hand, distearyl-pentaerythritol-diphosphite, di-(di-nonylphenyl)-mono-(p-nonylphenyl)-phosphite and the like not only are acceptable as the additive but also even improve reduction in yellow discoloration. Besides, sulfur antioxidants such as di-tetradecyl-3,3'-thio-dipropionate, di-stearyl-thio-di-propionate, lauryl-stearyl-thio-dipropionate, tetrakis(-methylene-3-dodecylthiopropionate)methane and the like may be added.

As examples of the polymer clarifiers and the nucleating agents are mentioned 1,3,2,4-dibenzylidenesorbitol which is a condensate of sorbitol and benzaldehyde and derivatives thereof with substituents such as alkyl groups such as methyl, ethyl, n-propyl, n-butyl, t-butyl and the like or alkoxyl groups such as methoxy, ethoxy, propoxy and the like on the benzene ring. Also are mentioned aluminum-p-t-butyl-benzoate, aromatic acid phosphate and the like.

The ultraviolet light absorbers include 2-hydroxy-4-n-octoxy-benzophenone, 2-(2'-hydroxy-3',5'-di-t-butyl-phenyl)-5-chlorobenzotriazole and the like.

Examples of the peroxides are benzoylperoxide, 1,3-bis-(t-butylperoxyisopropyl)benzene, 2,5-dimethyl-2,5-di-(t-butylperoxy)hexane and the like.

As the dispersing agent or the neutralizing agent are mentioned salts of stearic acid with a metal such as calcium, magnesium or sodium and the like.

Production of the compositions according to the present invention is carried out by adding to the polyolefins in powder or paste form the above-described essential components and, as needed, the other components and melt kneading the mixture in a kneader such as a roller, Brabender-plasticorder, extruder or the like.

In general, it is practical procedures that medical instruments such as syringe are prepared by adding each component to a powdered polyolefin, blending the mixture in an appropriate blending apparatus such as a mixer, melt kneading the blend through an extruder into pellets and molding the pellets by means of injection molding. Direct molding by blending the components may be employed.

EXAMPLE 1

To 100 parts of a powdered propylene-ethylene randam copolymer (Norblen MG3B manufactured by Mitsubishi Petrochemical Co., Ltd.; MFR 14 g./10 min., ethylene content 2.5% by weight) were added hindered amines, phenol compounds, antioxidants and other components as shown in the table below in incorporation as indicated in Table 1. The mixture was passed through an extruder 30 mm. in diameter at 210° C. to form pellets. The resulting pellets were molded in an injection molder at 280° C. To produce square sheets each $100 \times 100 \times 1$ mm. in size and outer cylinders for syringes each in 91 mm. length $\times$ 16 mm. inside diameter $\times$ 0.95 mm. thickness and having 10 ml. of volume. The sheets and the cylinders received a radiation dose of 2.5 Mrad from a cobalt-60 source and then tested.

The results are shown in Table 1.

The tests included determination of days to cracking and degree of yellow discoloration when placed in an oven at 120° C. and determination of energy at 50% breaking measured by means of a Dupont impact tester immediately after the gamma irradiation.

In addition, the specimens were tested for sterilization according to the Japan Pharmacopeia bacteriological sterilization test (B-32-1). No bacterial growth was observed, and the sterilization was confirmed.

Hindered Amine
(1) Sanol 770: Manufactured by Sankyo Co., Ltd., a compound of the formula [I] in which $l=8$ and $R_1=CH_3$.

Phenol Compound
(2) TPNC: Manufactured by ICI; a compound of the formula [III] in which $n=1$, $R_2=$t-butyl and $R_3=CH_3$ at 2-position.
(3) GR3114: Manufactured by Goodrich Chemicals, a compound of the formula [IV] in which $R_2=$t-butyl, $R_3=$t-butyl at 5-position and the OH group is at 4-position.

Antioxidants and Others
(4) PBK: Calcium stearate manufactured by Nitto Chemical Industry Co., Ltd.
(5) EC 1: 1,3,2,4-Dibenzylidenesorbitol manufactured by E.C. Chemical Industry.
(6) WX 618: Distearyl-pentaerythritol-diphosphite manufactured by Borg-Warner Corporation.
(7) 9,10-Dihydroanthracene (reagent).
(8) Seenox 412S: Tetrakis-(methylene-3-dodecylthiopropionate)methane manufactured by Shipro-Kasei Co., Ltd.
(9) DMTP: Dimyristylthiodipropionate manufactured by Yoshitomi Pharmaceutical Industries, Ltd.
(10) RA1010: Tetrakis-[methylene(3,5-di-t-butyl-4-hydroxyphenyl)propionate]methane manufactured by Ciba-Geigy.

TABLE 1

|  |  | Example | | | Comparative Example | | | |
| --- | --- | --- | --- | --- | --- | --- | --- | --- |
|  |  | 1 | 2 | 3 | 4 | 5 | 6 | 7 |
| Formula* | Sanol 770 | 0.20 | 0.20 | 0.20 | — | — | — | — |
|  | TPNC | — | — | 0.05 | — | — | — | — |
|  | GR 3114 | 0.05 | 0.05 | — | 0.05 | 0.05 | — | — |
|  | PBK | 0.05 | 0.05 | 0.05 | 0.05 | 0.05 | 0.05 | 0.05 |
|  | EC 1 | 0.18 | 0.18 | 0.18 | 0.18 | 0.18 | 0.18 | 0.18 |
|  | WX 618 | 0.05 | 0.05 | — | 0.05 | 0.05 | 0.03 | — |
|  | 9,10-Dihydroanthracene | — | 0.10 | — | — | — | — | — |
|  | Seenox 412S | — | — | — | 0.20 | — | — | — |
|  | DMTP | — | — | — | — | 0.15 | — | — |
|  | RA 1010 | — | — | — | — | — | 0.03 | 0.10 |
| Test | 120° C. Oven test (days) | >20 | >20 | >20 | 4 | >2 | — | — |
|  | Degree of | slight | slight | slight | slight | slight | moderate | remarkable |

TABLE 1-continued

| | Example | | | Comparative Example | | | |
|---|---|---|---|---|---|---|---|
| | 1 | 2 | 3 | 4 | 5 | 6 | 7 |
| yellow discoloration | | | | | | | |
| Dupont impact value (kg · cm) | 2 | 3 | 2 | 1 | — | — | — |

Note:
*Part by weight per 100 parts by weight of the polymer.

EXAMPLE 2

The base powdered resin in Example 1 was replaced

TABLE 2

| | Example | | | | | | | | | | Comparative Example | | | | |
|---|---|---|---|---|---|---|---|---|---|---|---|---|---|---|---|
| | 8 | 9 | 10 | 11 | 12 | 13 | 14 | 15 | 16 | 17 | 18 | 19 | 20 | 21 | 22 |
| Formula | | | | | | | | | | | | | | | |
| Sanol 770 | 0.05 | 0.10 | 0.05 | 0.05 | 0.05 | — | — | — | — | — | 0.05 | 0.10 | — | — | — |
| C10-622 | — | — | — | — | — | 0.05 | 0.05 | 0.05 | 0.05 | 0.05 | — | — | 0.05 | — | — |
| TPNC | — | — | 0.03 | — | — | — | 0.03 | 0.03 | 0.03 | 0.03 | — | — | — | — | 0.03 |
| GR 3114 | 0.03 | 0.03 | — | — | — | 0.03 | — | — | — | — | — | — | — | 0.03 | — |
| Mark 522 | — | — | — | 0.10 | — | — | — | — | — | — | — | — | — | — | — |
| Mark P | — | — | — | — | 0.10 | — | — | — | — | — | — | — | — | — | — |
| PBK | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| EC 1 | 0.18 | 0.18 | 0.18 | 0.18 | 0.18 | 0.18 | 0.18 | — | — | 0.18 | 0.18 | 0.18 | 0.18 | 0.18 | 0.18 |
| WX 618 | 0.03 | 0.03 | — | — | — | 0.03 | — | — | — | — | — | — | — | 0.03 | — |
| Gelall MD | — | — | — | — | — | — | — | 0.15 | — | — | — | — | — | — | — |
| Di-(p-n-butyl)-benzylidene)-sorbitol | — | — | — | — | — | — | — | — | 0.15 | — | — | — | — | — | — |
| Perkadox 14 | — | — | — | — | — | — | — | — | — | 0.015 | — | — | — | — | — |
| Test | | | | | | | | | | | | | | | |
| 120° C. Oven test (days) | >20 | >20 | >20 | >20 | >20 | >20 | >20 | >20 | >20 | >20 | >20 | >20 | >20 | <2 | <2 |
| Dupont impact value after heat treatment at 80° C. for 2 weeks (kg · cm) | >60 | >60 | >60 | 50 | 45 | >60 | >60 | >60 | >60 | >60 | 20 | 23 | 35 | — | — |

Note: *Part by weight per 100 parts by weight of the polymer by a propylene-ethylene random copolymer with an MFR of 6 g./10 min. and an ethylene content of 2.5% by weight (trial product). Compositions thereof with the additives incorporated as shown in Table 2 were molded and tested after the gamma irradiation in the same way as in Example 1. Results are shown in Table 2.

Additives other than those employed in Example 1 were employed as shown in the table below.
Hindered Amine
(1) C10–622: Manufactured by Sankyo Co., Ltd., a compound of the formula [II] in which m=4 and $R_1=CH_3$.

Phosphorous ester of phenol
(2) Mark 522: Manufactured by Adeka Argus Chemical Co., Ltd., mainly containing a compound of the formula [V] in which n=1, $R_2$=t-butyl, $R_3$=$CH_3$ at 2-position and $R_4$=$C_{13}H_{27}$.
(3) Mark P: Manufactured by Adeka Argus Chemical Co., Ltd., mainly containing a compound of the formula [VI] in which $R_2$=t-butyl, $R_3$=$CH_3$ at 2-position, $R_4$=$C_{13}H_{27}$ and $R_5$=$C_3H_7$.

Other Additives
(4) Gelall MD: Di-(p-methylbenzylidene)sorbitol manufactured by New Japan Chemical Co., Ltd.
(5) Di-(p-n-butylbenzylidene)sorbitol (reagent).

(6) Perkadox 14: 1,3-Bis(t-butylperoxyisopropyl)benzene manufactured by Kayaku Noury Corporation.

What we claim is:

1. A medical instrument sterilized by gamma irradiation made from a polyolefin composition which is resistant to gamma irradiation comprising (i) a polyolefin, (ii) from 0.01 to 1 part by weight per 100 parts by weight of said polyolefin of a hindered amine compound represented by the formula II below and (iii) from 0.01 to 1 part by weight per 100 parts by weight of said polyolefin of a phenol or phosphorous ester thereof represented by any one of the formulae III—VI below

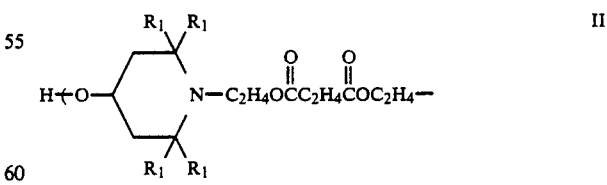

II

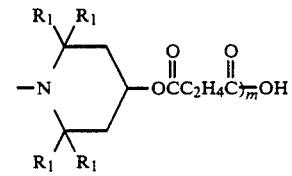

-continued

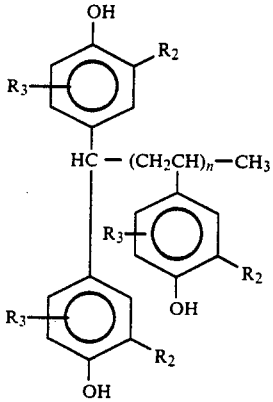

III

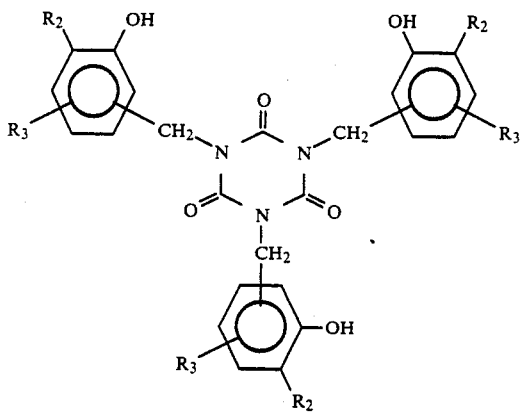

IV

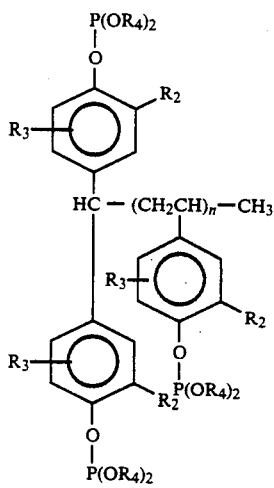

V

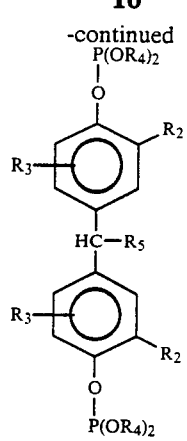

VI wherein $R_1$ and $R_3$ represent an alkyl group containing from 1 to 18 carbon atoms respectively, $R_2$ and $R_5$ represents an alkyl group containing from 1 to 8 carbon atoms respectively, $R_4$ represents an alkyl group containing from 1 to 30 carbon atoms, l is an integer from 0 to 30, m is an integer from 1 to 40, and n is an integer from 1 to 6.

2. The medical instrument of claim 1 wherein said medical instrument is a syringe.

3. The medical instrument of claim 1 or 2 wherein said polyolefin is a propylene polymer.

4. The medical instrument of claim 3 wherein said propylene polymer is an ethylene-propylene copolymer.

5. The medical instrument of claim 1 or 2 wherein said hindered amine compound is represented by the formula II and wherein n is 4 and $R_1$ is methyl.

6. The medical instrument of claim 1 or 2 wherein said phenol represented by the formula III wherein n is 1, $R_2$ is t-butyl and $R_3$ is methyl at 2-position.

7. The medical instrument of claim 1 or 2 wherein said phenol or phosphorous ester thereof is represented by the formula IV and wherein $R_2$ is t-butyl, $R_3$ is t-butyl at the 5-position and the OH group is at 4-position.

8. The medical instrument of claim 1 or 2 wherein said phenol or phosphorous ester thereof is represented by the formula V and wherein n is 1, $R_2$ is t-butyl, $R_3$ is methyl at the 2-position and $R_4$ is $-C_{13}H_{27}$.

9. The medical instrument of claim 1 or 2 wherein said phenol or phosphorous ester thereof is represented by the formula VI wherein $R_2$ is t-butyl, $R_3$ is methyl at the 2-position, $R_4$ is $-C_{13}H_{27}$ and $R_5$ is $-C_3H_7$.

10. The medical instrument of claim 1 or 2 wherein said hindered amine compound (ii) and said phenol or the phosphorous ester thereof (ii) are each in an amount of from 0.01 to 0.5 part by weight per 100 parts by weight of the polyolefin.

11. The medical instrument of claim 1 or 2 wherein said hindered amine compound is selected from the group represented by the formula II wherein n is 4 and $R_1$ is methyl; and wherein said phenol or phosphorous ester thereof is selected from those represented by the formula III wherein n is 1, $R_2$ is t-butyl and $R_3$ is methyl at 2-position; by the formula IV and wherein $R_2$ is t-butyl, $R_3$ is t-butyl at the 5-position and the OH group is at 4-position; by the formula V and wherein n is 1, $R_2$ is t-butyl, $R_3$ is methyl at the 2-position and $R_4$ is $-C_{13}H_{27}$; and by the formula VI wherein $R_2$ is t-butyl, $R_3$ is methyl at the 2-position, $R_4$ is $-C_{13}H_{27}$ and $R_5$ is $-C_3H_7$; and wherein said polyolefin is a propylene polymer.

12. The medical instrument of claim 11 wherein said hindered amine compound (ii) and said phenol or the phosphorous ester thereof (ii) are each in an amount of from 0.01 to 0.5 part by weight per 100 parts by weight of the polyolefin.

* * * * *

UNITED STATES PATENT AND TRADEMARK OFFICE
CERTIFICATE OF CORRECTION

PATENT NO. : 4,569,736
DATED      : February 11, 1986
INVENTOR(S): Kimiho KOSEGAKI et al It is certified that error appears in the above-identified patent and that said Letters Patent is hereby corrected as shown below:

TITLE PAGE, left column, between the filing data and the Related U.S. Application Data, insert the following priority data:

--[30]   Foreign Application Priority Data

Sept. 19, 1981   [JP]   Japan ........ 56-148384--.

TITLE PAGE, right column, ABSTRACT, line 1, change

"YMedical" to --Medical--.

Signed and Sealed this

Tenth Day of February, 1987

Attest:

DONALD J. QUIGG

Attesting Officer

Commissioner of Patents and Trademarks